United States Patent [19]
Distler et al.

[11] 4,134,889
[45] * Jan. 16, 1979

[54] MANUFACTURE OF GLYCINONITRILES

[75] Inventors: Harry Distler, Bobenheim; Erwin Hartert; Helmut Schlecht, both of Ludwigshafen, all of Fed. Rep. of Germany

[73] Assignee: BASF Aktiengesellschaft, Ludwigshafen, Fed. Rep. of Germany

[*] Notice: The portion of the term of this patent subsequent to May 10, 1994, has been disclaimed.

[21] Appl. No.: 792,727

[22] Filed: May 2, 1977

[30] Foreign Application Priority Data

May 8, 1976 [DE] Fed. Rep. of Germany ....... 2620445
May 11, 1976 [DE] Fed. Rep. of Germany ....... 2620743

[51] Int. Cl.² ........................................... C07C 120/00
[52] U.S. Cl. ................................. 260/239 B; 546/246; 546/145; 260/315; 260/319.1; 260/326.1; 260/326.11 R; 260/326.62; 260/464; 260/465 E; 260/465.5 R; 260/465.5 A; 544/102; 544/163; 544/402; 548/300; 548/333; 548/341; 548/356; 548/372; 548/378; 548/379
[58] Field of Search ............ 260/464, 465 E, 465.5 R, 260/465.5 A, 239 B

[56] References Cited
U.S. PATENT DOCUMENTS
4,022,815  5/1977  Schlecht et al. .............. 260/465.5 A Primary Examiner—Joseph Paul Brust
Attorney, Agent, or Firm—Keil, Thompson & Shurtleff

[57] ABSTRACT

Manufacture of glycinonitriles by reacting amines with carbonyl compounds and hydrogen cyanide under specific reaction conditions in respect of the temperature, reaction time and hydrogen cyanide concentration.

The glycinonitriles obtainable by the process of the invention are antioxidants and valuable starting materials for the manufacture of dyes, fungicides, bactericides, textile auxiliaries and inhibitors for use in antifreezes.

13 Claims, No Drawings

MANUFACTURE OF GLYCINONITRILES

The present invention relates to a process for the manufacture of glycinonitriles by reacting amines with carbonyl compounds and hydrogen cyanide under specific reaction conditions in respect of the temperature, reaction time and hydrogen cyanide concentration.

German Patent No. 656,350 discloses that glycollic acid nitrile can be reacted with excess methylamine in aqueous solution under pressure, to give sarcosinonitrile. An excess of up to 10 moles of methylamine per mole of hydroxyacetonitrile is recommended in order to achieve good yields of sarcosinonitrile (German Patent No. 656,350). If stoichiometric amounts are used, considerable amounts of the nitrile of methyldigylcollamic acid are formed, and this compound is difficult to remove.

Another method or preparation of N-alkyl-substituted glycinonitriles uses formaldehyde, in the presence of sodium bisulfite compounds, as the starting material, the aldehyde being reacted with sodium cyanide and aliphatic amines. Using sodium cyanide and sodium bisulfite presents environmental problems when the method is carried out industrially, on account of the formation of alkali metal salts, which may contain residual cyanides, as by-products. The use of the amines in the form of salts, e.g. hydrochlorides has also already been proposed (Jean Mathieu and Jean Weil-Raynal, Formation of C—C Bonds, volume I, pages 442–446 (Georg Thieme Verlag, Stuttgart 1973)).

All these methods are unsatisfactory from the point of view of simple and economical operation, good yields of end product and ease of working up and in particular in respect of protection of the environment and purification of waste water.

German Laid-Open Application DOS 1,543,342 discloses the continuous reaction of aniline with formaldehyde and hydrogen cyanide at from 80 to 130° C, followed by hydrolysis of the reaction mixture with alkali metal hydroxide. Phenylglycinonitrile itself is not isolated. The patent application states that in general less than 10%, and frequently only from 1 to 5%, of the hydrogen cyanide and the formaldehyde are present in the free form in the reaction mixture. In none of the Examples is free hydrogen cyanide used.

We have found that glycinonitriles of the formula

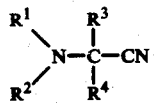

where $R^1$, $R^2$, $R^3$ and $R^4$ may be identical or different and each is an aliphatic, cycloaliphatic or araliphatic radical, $R^3$ and $R^4$ may also each be an aromatic radical, $R^2$ and/or $R^4$ may in addition also be hydrogen, $R^1$ and $R^2$ together with the adjacent nitrogen may also be members of a heterocyclic radical, $R^3$ and $R^4$ may also simultaneously each be hydrogen, provided that $R^1$ and/or $R^2$ are a cycloaliphatic or an araliphatic radical or $R^1$ and $R^2$ together with the adjacent nitrogen are members of a heterocyclic radical, are obtained in an advantageous manner if amines of the formula

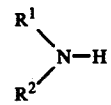

where $R^1$ and $R^2$ have the above meaning, are reacted with carbonyl compounds of the formula

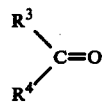

where $R^3$ and $R^4$ have the above meaning, and with hydrogen cyanide in the presence of water for from 0.1 to 4 hours at from 0 to 80° C, the concentration of hydrogen cyanide during the reaction not exceeding 0.1 percent by weight, based on the reaction mixture.

Where acetone and piperidine are used, the reaction may be represented by the following equation:

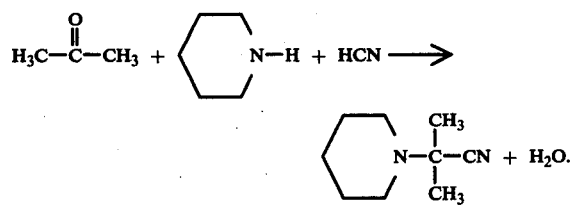

Where piperidine and formaldehyde are used, the reaction may be represented by the following equation:

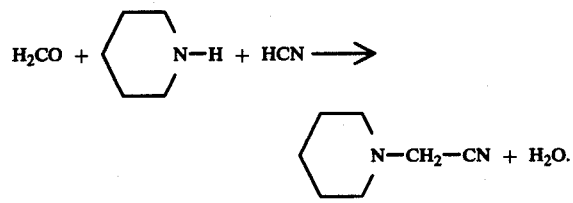

Compared with the prior art the process of the invention gives glycinonitriles more simply and more economically, in better yield and higher purity. The process is particularly suitable for operation on an industrial scale and for continuous operation, presents no substantial waste water problems and gives virtually no resinous by-products which are preferentially formed at fairly high reaction temperatures due to the presence of formaldehyde and at fairly high hydrogen cyanide concentrations, or may be formed because of the presence of aldehydes or ketones. All these advantageous properties are surprising in view of the prior art.

Compared with the process disclosed in German Laid-Open Application DOS No. 1,543,342, the process of the invention also gives cycloaliphatic, araliphatic or heterocyclic glycinonitriles more simply and more economically, in better yield and higher purity.

Formaldehyde may be used in the liquid form or as a gas, but is in general used in the form of its aqueous solution, advantageously of from 10 to 50 percent strength by weight and preferably of from 30 to 40 percent strength by weight. Hydrogen cyanide may be used as the gas or, advantageously, in the liquid form or in aqueous solution. The starting amine II may be used by itself or in solution; an aliphatic starting amine II in advantageously used in aqueous solution. The use of solutions of from 40 to 60 percent strength by weight is advantageous. The three starting materials may be reacted in stoichiometric amount, or with any of the components in excess; preferably the conditions correspond to an excess, over the stoichiometric amount, of from 0.1 to 5 moles of amine, preferably from 0.1 to 2 moles of amine in the case of aliphatic amines and from 0.5 to 1 mole of amine in the case of nonaliphatic amines, and/or an excess of from 0.01 to 0.1 mole of hydrogen cyanide per mole of carbonyl compound III.

Preferred starting materials II and III and accordingly preferred end products I are those where $R^1$, $R^2$, $R^3$ and $R^4$ may be identical or different and each is alkyl of 1 to 20, preferably of 1 to 8, and especially of 1 to 4, carbon atoms, or alkenyl of 2 to 20, preferably of 2 to 8, carbon atoms, cycloalkyl of 5 to 8 carbon atoms or aralkyl of 7 to 12 carbon atoms, $R^3$ and $R^4$ may also each be phenyl or naphthyl, $R^2$ and/or $R^4$ may in addition each be hydrogen, $R^1$ and $R^2$ together with the adjacent nitrogen may also be members of a 5-membered or 6-membered heterocyclic radical which may contain a further nitrogen or an oxygen, $R^3$ and $R^4$ may also simultaneously each be hydrogen, provided that $R^1$ and/or $R^2$ are a cycloaliphatic or an araliphatic radical or $R^1$ and $R^2$ together with the adjacent nitrogen are members of a heterocyclic radical. The above rings or radicals may in addition be substituted by groups and/or atoms which are inert under the reaction conditions, e.g. alkyl or alkoxy each of 1 to 4 carbon atoms, or hydroxyl, nitro or cyano.

Examples of suitable starting materials II are methylamine, ethylamine, n-propylamine, isopropylamine, n-butylamine, isobutylamine, sec.-butylamine, tert.-butylamine, pentylamine, pentyl-2-amine, pentyl-3-amine, n-hexylamine, n-heptylamine, n-octylamine, n-nonylamine, n-decylamine, n-tridecylamine, n-octadecylamine, oleylamine, 2-ethylhexylamine, 2-ethylpentylamine, 3-ethylpentylamine and 4-methylheptylamine; dimethylamine, diethylamine, di-n-propylamine, diisopropylamine, di-n-butylamine, diisobutylamine, di-sec.-butylamine, di-tert.-butylamine, dipentylamine, di-(pentyl-2)-amine, di-(pentyl-3)-amine, di-n-hexylamine, di-n-heptylamine, di-n-octylamine, di-n-nonylamine, di-n-decylamine, di-2-ethylhexylamine and di-4-methylheptylamine; corresponding amines with 2 of the above radicals which, however, are different from one another, e.g. methylethylamine; cyclohexylamine, cyclopentylamine, cycloheptylamine, benzylamine and phenylethylamine; dicyclohexylamine, dicyclopentylamine, dicycloheptylamine, dibenzylamine and diphenylethylamine; pyrrolidine, $\Delta^2$-pyrroline, $\Delta^3$-pyrroline, pyrrole, pyrazole, pyrazoline, prazolidine, imidazolidine, hexamethyleneimine, pentamethyleneimine, 3-imidazoline, piperidine, morpholine, piperazine, indoline, indole, isoindoline, isoindole, indazole, benzimidazole, 1,2,3,4-tetrahydroisoquinoline, carbazole, phenoxazine, 4-methylimidazole, 2-methylindole, 3-methylindole, 2-methylpiperazine, 3-methylpyrrole, 2-methylpyrrole, N-ethylmorpholine, 2-ethylpiperidine and 2-methylpyrrolidine.

The following are examples of suitable starting materials III: formaldehyde, acetaldehyde, propionaldehyde, n-butyraldehyde, isobutyraldehyde, 2-methylbutyraldehyde, 2-ethylcapronaldehyde, n-valeraldehyde, isovaleraldehyde, 2,2-dimethylpropionaldehyde, 2,2-dimethyl-3-hydroxypropionaldehyde, n-capronaldehyde, iso-capronaldehyde, 2-methylvaleraldehyde, 3-methylvaleraldehyde, 2-ethylbutyraldehyde, 2,2-dimethylbutyraldehyde, 2,3-dimethylbutyraldehyde, 3,3-dimethylbutyraldehyde, enanthaldehyde, 2-methylcapronaldehyde, 3-methylcapronaldehyde, 4-methylcapronaldehyde, 5-methylcapronaldehyde, 2-ethylvaleraldehyde, 2,2-dimethylvaleraldehyde, 3-ethylvaleraldehyde, 3,3-dimethylvaleraldehyde, 2,3-dimethylvaleraldehyde, 4-ethylvaleraldehyde, 4,4-dimethylvaleraldehyde, 3,4-dimethylvaleraldehyde, 2,4-dimethylvaleraldehyde, 2-ethyl-2-methylbutyraldehyde, 2-ethyl-3-methylbutyraldehyde, cyclohexanealdehyde, benzaldehyde, phenylacetaldehyde, acetone, methyl ethyl ketone, methyl n-propyl ketone, methyl isopropyl ketone, methyl n-butyl ketone, methyl isobutyl ketone, methyl sec.-butyl ketone, methyl tert.-butyl ketone, methyl n-pentyl ketone, methyl pentyl-2 ketone, methyl pentyl-3 ketone, methyl isoamyl ketone, methyl (2-methyl)-butyl ketone, methyl (1-methyl)-butyl ketone, methyl (2-ethyl)-butyl ketone, methyl (3-ethyl)-butyl ketone, methyl (2,2-dimethyl)-butyl ketone, methyl (2,3-dimethyl)-butyl ketone and methyl (3,3-dimethyl)-butyl ketone; corresponding unsymmetrical ketones which contain phenyl, benzyl, cyclohexyl, ethyl, n-propyl, isopropyl or n-butyl instead of methyl; diethyl ketone, di-n-propyl ketone, di-isopropyl ketone, di-n-butyl ketone, di-isobutyl ketone, di-sec.-butyl ketone, di-tert.-butyl ketone, di-n-pentyl ketone, dipentyl-2 ketone, dipentyl-3 ketone, diisoamyl ketone, di-(2-methyl)-butyl ketone, di-(1-methyl)-butyl ketone, di-(2-ethyl)-butyl ketone, di-(3-ethyl)-butyl ketone, di-(2,2-dimethyl)-butyl ketone, di-(2,3-dimethyl)-butyl ketone, di-(3,3-dimethyl)-butyl ketone, dicyclohexyl ketone, dibenzyl ketone and benzophenone.

The reaction is carried out at from 0 to 80° C, advantageously from 20 to 80° C, preferably from 30 to 65° C, and in the case of formaldehyde as the carbonyl compound III preferably from 10 to 65° C and especially from 15 to 40° C, under reduced pressure, superatmospheric pressure or, preferably, atmospheric pressure, batchwise or, preferably, continuously. Water is advantageously used in the form of aqueous amine solutions and in addition water is formed in the reaction itself; in total, from 1 to 6, preferably from 3 to 4, moles of water, based on per mole of compound III may be used. Hydrogen cyanide is added to the starting mixture, before and during the reaction, in amounts such that the concentration, based on the reaction mixture during the reaction, does not exceed 0.1, and preferably is from 0.01 to 0.1 and especially from 0.05 to 0.1 percent by weight. The reaction time (or, in continuous operation, the residence time) is from 0.1 to 4 hours, preferably from 1 to 2 hours. The use of water as the sole solvent is preferred, but organic solvents which are inert under the reaction conditions may also be present. Examples of suitable solvents are aromatic hydrocarbons, e.g. toluene, benzene, ethylbenzene, o-, m- and p-xylene, isopropylbenzene and methylnaphthalene; aliphatic or cyclialiphatic hydrocarbons, e.g. heptane, α-pinene, pinane, nonane, gasoline fractions within a boiling range of from 70 to 190° C, cyclohexane, methylcyclohexane, petroleum ether, decaline, hexane, naphtha, 2,2,4-trimethylpentane, 2,2,3-trimethylpentane, 2,3,3-trimethylpentane and octane; and corresponding mixtures. The solvent is advantageously used in amounts of from 40 to 10,000 percent by weight, preferably from 50 to 1,500 percent by weight, based on starting material III.

The reaction may be carried out as follows: a mixture of compound III, water, hydrogen cyanide and starting amine II, with or without an organic solvent, is kept at the reaction temperature for the reaction time. Some of the hydrogen cyanide is introduced into the starting mixture and some is added during the reaction, in portions or continuously, so that the above concentration of hydrogen cyanide is maintained during the entire reaction time. The continuous measurement of the hydrogen cyanide concentration is advantageously carried out by means of a silver/calomel electrode. The end product is then isolated from the reaction mixture by conventional methods, e.g. by distillation or by extraction, e.g. with cyclohexane or ethyl acetate, followed by distillation of the solvent.

The glycinonitriles obtainable by the process of the invention are antioxidants and valuable starting materials for the manufacture of dyes, fungicides, bactericides, textile auxiliaries and inhibitors for use in antifreezes.

On hydrolysis, e.g. with alkali metal hydroxide solutions, they give alkali metal salts of the corresponding glycine, which are selective absorbents for $CO_2$, $SO_2$ and $H_2S$.

Hydrogenation of the glycinonitriles gives asymmetrical diamines which are valuable starting materials for drugs and crop protection agents.

In the Examples which follow, parts are by weight.

EXAMPLE 1

Per hour, 1,530 parts of piperidine, 1,044 parts of acetone, 300 parts of water and 486 parts of liquid hydrogen cyanide are slowly mixed in a stirred kettle at 30° C; during the reaction the hydrogen cyanide concentration does not exceed 0.1 percent by weight, based on the total mixture, and averages 0.085 percent by weight. The mixture is allowed to react for a further 3 hours at 65° C in a downstream kettle. The total reaction time is 3.8 hours. The mixture is then cooled and extracted with 1,000 parts of ethyl acetate, and the latter is distilled off. 2,710 parts (99% of theory) of piperidino-α-(dimethyl)-glycinonitrile, of melting point 37–38° C, are obtained per hour.

EXAMPLE 2

Per hour, 1,530 parts of piperidine, 1,908 parts of benzaldehyde, 100 parts of water and 486 parts of hydrogen cyanide are slowly mixed in a stirred kettle at 65° C; during the reaction the hydrogen cyanide concentration does not exceed 0.1 percent by weight, based on the total mixture, and averages 0.085 percent by weight. Using the method described in Example 1, 3,590 parts (99% of theory) of piperidino-α-(phenyl)-glycinonitrile of melting point 54–57° C are obtained per hour.

EXAMPLE 3

Using the method described in Example 1, 1,530 parts of piperidine, 500 parts of water, 1,296 parts of n-butyraldehyde and 486 parts of liquid hydrogen cyanide per hour are slowly mixed in a stirred kettle at 27° C; during the reaction the hydrogen cyanide concentration does not exceed 0.1 percent by weight, based on the total mixture, and averages 0.085 percent by weight. The mixture is allowed to react for a further 2 hours at 30° C in a downstream kettle. The total reaction time is 3 hours. The upper organic phase which forms is separated off and distilled. Per hour, 2980 parts (99% of theory) of piperidino-α-(propyl)-glycinonitrile of boiling point 52° C/0.02 mbar, and with $n_D^{20} = 1.4617$, are obtained.

EXAMPLE 4

Using the method described in Example 1, 370 parts of n-dodecylamine, 212 parts of benzaldehyde, 50 parts of water and 54 parts of hydrogen cyanide per hour are slowly mixed in a stirred kettle at 45° C; during the reaction the hydrogen cyanide concentration does not exceed 0.1 percent by weight, based on the total mixture, and averages 0.085 percent by weight. The mixture is allowed to react for a further 2 ½ hours at 55° C in a downstream kettle. The total reaction time is 3 ½ hours. The upper organic phase which has formed is separated off at 55° C, and is distilled. Following the method described in Example 1, 586 parts (97% of theory) of α-phenyl-N-n-dodecyl-aminoacetonitrile, with $n_D^{20} = 1.4928$, are obtained per hour.

EXAMPLE 5

Using the method described in Example 1, 370 parts of n-dodecylamine, 144 parts of n-butyraldehyde, 50 parts of water and 54 parts of liquid hydrogen cyanide per hour are slowly mixed in a stirred kettle at 55° C; during the reaction the hydrogen cyanide concentration does not exceed 0.1 percent by weight, based on the total mixture, and averages 0.085 percent by weight. The mixture is allowed to react for a further 2 ½ hours at 50° C in a downstream kettle. The total reaction time is 3 ½ hours. The organic upper phase is separated off. After extraction with 300 parts of ethyl acetate, using the method described in Example 1, 520 parts (97% of theory) of α-n-dodecylamino-α-n-propylacetonitrile, with $n_D^{20} = 1.4505$, are obtained.

EXAMPLE 6

Per hour, 400 parts of a 30 percent strength by weight aqueous formaldehyde solution, 108 parts of hydrogen cyanide and 340 parts of piperidine are slowly mixed in a stirred kettle at 20° C; during the reaction the hydrogen cyanide concentration does not exceed 0.1 percent by weight, based on the total mixture, and averages from 0.08 to 0.09 percent by weight. The total reaction time is one hour. Per hour, 848 parts of reaction mixture are obtained. This mixture separates into 2 phases, and after separating off the organic phase 485 parts of piperidinylglycinonitrile (98% of theory) of boiling point 98° C/18 mm Hg, and with $n_D^{20} = 1.4592$, are obtained.

EXAMPLE 7

400 parts of a 30 percent strength by weight aqueous formaldehyde solution, 108 parts of hydrogen cyanide and 396 parts of cyclohexylamine are slowly mixed in a stirred vessel at 25° C; during the reaction the hydrogen cyanide concentration does not exceed 0.1 percent weight, based on the total mixture, and averages 0.08 percent by weight. The total reaction time is one hour. Per hour, 532 parts of cyclohexylglycinonitrile (96% of theory), of $n_D^{20} = 1.4670$, are obtained by the method described in Example 6.

EXAMPLE 8

Using the method described in Example 6, 1,566 parts of morpholine, 1,800 parts of a 30 percent strength by weight aqueous formaldehyde solution and 486 parts of liquid hydrogen cyanide per hour are mixed in a stirred kettle at 18° C; the hydrogen cyanide concentration does not exceed 0.1 percent by weight, based on the total mixture, and averages 0.08 percent by weight. In a downstream reaction vessel, the mixture is allowed to continue to react for a further hour at 30° C. The total reaction time is 2 hours. After cooling to 0° C, N-morpholinylglycinonitrile precipitates, and is filtered off. Per hour, 1,810 parts of N-morpholinylglycinonitrile (80% of theory) of melting point 55–57° C are obtained.

EXAMPLE 9

Using the method described in Example 6, 1,278 parts of pyrrolidine, 1,800 parts of a 30 percent strength by weight aqueous formaldehyde solution and 486 parts of liquid hydrogen cyanide per hour are mixed in a stirred kettle at 20° C; the hydrogen cyanide concentration does not exceed 0.1 percent by weight, based on the total mixture, and averages 0.08 percent by weight. The mixture is allowed to react for a further hour at 45° C. The total reaction time is 2 hours. The reaction mixture is heated at 60° C and at the same time 350 parts of sodium carbonate are added. After removing the organic phase 1,910 parts, per hour of N-pyrrolidinoglycinonitrile (95% of theory) of boiling point 111° C/60 mm Hg and with $n_D^{20} = 1.4557$ are obtained.

EXAMPLE 10

Using the method described in Example 6, 214 parts of benzylamine, 200 parts of a 30 percent strength by weight aqueous formaldehyde solution and 54 parts of liquid hydrogen cyanide per hour are mixed in a stirred kettle at 20° C; the hydrogen cyanide concentration does not exceed 0.1 percent by weight, based on the total mixture, and averages 0.08 percent by weight. The reaction mixture is then allowed to react for a further hour at 45° C. The total reaction time is 2 hours. The organic lower phase is separated off, and 281 parts (96% of theory) of benzylglycinonitrile are obtained per hour, in the form of a colorless liquid of boiling point 111–114° C/0.4 mm Hg and with $n_D^{20} = 1.5362$.

We claim:

1. A process for the manufacture of a glycinonitrile of the formula

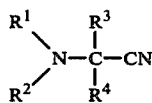
I wherein:
$R^1$, $R^2$, $R^3$ and $R^4$ may be identical or different unsubstituted radicals and each is alkyl of 1 to 20 carbon atoms, alkenyl of 2 to 20 carbon atoms, cycloalkyl of 5 to 8 carbon atoms or aralkyl of 7 to 12 carbon atoms;
$R^3$ and $R^4$ may also each be phenyl or naphthyl;
$R^2$ or $R^4$ may in addition each be hydrogen; $R^1$ and $R^2$ together with the adjacent nitrogen may also represent a 5-membered or 6-membered heterocyclic radical which may contain a further nitrogen or oxygen atom in the ring;
$R^3$ and $R^4$ each may also simultaneously be hydrogen, provided that $R^1$ and $R^2$ each is a cylcoalkyl or an aralkyl radical or $R^1$ and $R^2$ together with the adjacent nitrogen represent a heterocyclic radical;
and wherein each of the above radicals may in addition be substituted by alkyl or alkoxy, each of 1 to 4 carbon atoms, or by hydroxyl, nitro or cyano, which process comprises:
reacting an amine of the formula

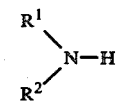
II where $R^1$ and $R^2$ have the above meaning, with a carbonyl compound of the formula

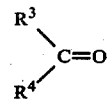
III where $R^3$ and $R^4$ have above meaning, and with hydrogen cyanide in the presence of water for from 0.1 to 4 hours at from 0 to 80° C, the concentration of hydrogen cyanide during the reaction not exceeding 0.1 percent by weight, based on the reaction mixture.

2. A process as claimed in claim 1, in which the reaction is carried out with an excess, over the stoichiometric amount, of from 0.1 to 5 moles of amine per mole of carbonyl compound III.

3. A process as claimed in claim 1, in which the reaction is carried out with an excess, over the stoichiometric amount, of from 0,1 to 2 moles of amine per mole of carbonyl compound III.

4. A process as claimed in claim 1, in which the reaction is carried out with an excess, over the stoichiometric amount, of from 0.5 to 1 mole of amine per mole of carbonyl compound III.

5. A process as claimed in claim 1, in which the reaction is carried out with an excess, over the stoichiometric amount, of from 0.01 to 0.1 mole of hydrogen cyanide per mole of carbonyl compound III.

6. A process as claimed in claim 1, in which the reaction is carried out at from 20 to 80° C.

7. A process as claimed in claim 1, in which the reaction is carried out at from 10 to 65° C.

8. A process as claimed in claim 1, in which the reaction is carried out at from 30 to 65° C.

9. A process as claimed in claim 1, in which the reaction is carried out at from 15 to 40° C.

10. A process as claimed in claim 1, in which the reaction is carried out with a total amount of from 1 to 6 moles of water per mole of carbonyl compound III.

11. A process as claimed in claim 1, in which the reaction is carried out with a concentration, during the reaction, of from 0.01 to 0.1 percent by weight of hydrogen cyanide, based on the reaction mixture.

12. A process as claimed in claim 1, in which the reaction is carried out with a concentration, during the reaction, of from 0.05 to 0.1 percent by weight of hydrogen cyanide, based on the reaction mixture.

13. A process as claimed in claim 1, in which the reaction is carried out for from 1 to 2 hours.

* * * * *